(12) United States Patent
Antwiler (10) Patent No.: US 8,841,122 B2
(45) Date of Patent: Sep. 23, 2014

(54) SYSTEMS AND METHODS FOR EXPANDING HIGH DENSITY NON-ADHERENT CELLS

(75) Inventor: Glen Delbert Antwiler, Lakewood, CO (US)

(73) Assignee: Terumo BCT, Inc., Lakewood, CO (US)

(*) Notice: Subject to any disclaimer, the term of this patent is extended or adjusted under 35 U.S.C. 154(b) by 0 days.

(21) Appl. No.: 13/473,271

(22) Filed: May 16, 2012

(65) Prior Publication Data

US 2012/0295352 A1    Nov. 22, 2012

Related U.S. Application Data (60) Provisional application No. 61/487,086, filed on May 17, 2011.

(51) Int. Cl.
   *C12N 5/00*      (2006.01)
   *C12M 1/00*      (2006.01)
   *C12M 1/12*      (2006.01)

(52) U.S. Cl.
   CPC ............... *C12M 25/12* (2013.01); *C12M 29/16* (2013.01); *C12M 23/58* (2013.01); *C12M 23/02* (2013.01)
   USPC ...................................... 435/325; 435/289.1

(58) Field of Classification Search
   USPC .............................................. 435/325, 289.1
   See application file for complete search history.

(56) References Cited

U.S. PATENT DOCUMENTS

| | | | |
|---|---|---|---|
| 4,032,407 A | 6/1977 | Scott et al. | |
| 4,885,087 A | 12/1989 | Kopf | |
| 4,918,019 A | 4/1990 | Guinn | |
| 4,978,616 A | 12/1990 | Dean, Jr. et al. | |
| 5,270,189 A | 12/1993 | Scott | |
| 5,622,857 A | 4/1997 | Goffe | |
| 5,728,581 A | 3/1998 | Schwartz et al. | |
| 5,998,184 A | 12/1999 | Shi | |
| 6,642,019 B1 | 11/2003 | Anderson et al. | |
| 7,598,075 B2 | 10/2009 | Smith et al. | |
| 2003/0054544 A1 | 3/2003 | Gruenberg | |
| 2008/0220522 A1* | 9/2008 | Antwiler | 435/378 |
| 2008/0220523 A1 | 9/2008 | Antwiler | |
| 2009/0042253 A1 | 2/2009 | Hiller | |

FOREIGN PATENT DOCUMENTS

| | | |
|---|---|---|
| DE | 10211106 A1 | 10/2003 |
| EP | 0480400 A2 | 4/1992 |
| WO | 86/00636 A1 | 1/1986 |
| WO | 2009/037462 A1 | 3/2009 |

OTHER PUBLICATIONS

International Search Report and Written Opinion, PCT/US2012/038156, Nov. 22, 2012.

* cited by examiner

*Primary Examiner* — Karen Cochrane Carlson
*Assistant Examiner* — Natalie Moss
(74) *Attorney, Agent, or Firm* — Elizabeth J. Reagan; John R. Merkling; René A. Pereyra (57) ABSTRACT

Embodiments described herein generally relate to systems and methods for promoting the expansion of high density non-adherent cells through the use of a cell growth chamber, a mass transfer device, and a fluid circulation loop. Improved cell growth is achieved in the cell growth chamber by using a chamber having a particular orientation and shape, e.g., conical, to create a media-rich reservoir for growing cells. By placing the chamber in a vertical position, the force of media flow along the chamber walls is substantially equal and opposite to the gravitational force on the cells. The interaction of these forces maintains the non-adherent cells in suspension. The use of the cell growth chamber in conjunction with the mass transfer device and fluid circulation loop(s) creates efficiencies by relying on the cumulative and combined features of the devices.

25 Claims, 4 Drawing Sheets

SYSTEMS AND METHODS FOR EXPANDING HIGH DENSITY NON-ADHERENT CELLS

CROSS-REFERENCE TO RELATED APPLICATION

This application claims the benefit of U.S. Provisional Application Ser. No. 61/487,086, filed on May 17, 2011, and entitled, "A System for Expanding High Density Non-Adherent Cells." The disclosure of the above-identified application is hereby incorporated by reference in its entirety as if set forth herein in full for all that it teaches and for all purposes.

BACKGROUND

Cell expansion systems can be used to grow stem cells, as well as other types of cells, both adherent and non-adherent. Adherent cells require a surface for the cells to attach to before they will grow and divide. Non-adherent cells will grow and divide while floating in suspension.

Cell expansion systems provide nutrients to the growing cells and remove metabolites, as well as furnish a physiochemical environment conducive to cell growth. Cell expansion systems are known in the art.

As a component of a cell expansion system, a bioreactor, or cell growth chamber, plays an important role in providing an optimized environment for the expanding cells. There are many types of bioreactors known in the art. Bioreactor devices include culture flasks, roller bottles, shaker flasks, stirred-tank reactors, air-lift reactors, and hollow fiber bioreactors.

SUMMARY

Embodiments of the present disclosure generally relate to providing an environment conducive to high density non-adherent cell growth. Numerous factors may influence cell growth, including, for example, temperature, the geometries of the cells, etc. In particular, non-adherent cells expand based at least in part on the amount, or volume, of cell growth media available to them, in which increasing volumes of media promote increased cell growth. Cell density may affect not only the ability of cells to grow, but also the cell characteristics themselves. Therefore, if large amounts, or numbers, of non-adherent cells are desired, a large amount, or volume, of fluid should generally be available.

Aspects of particular embodiments provide for the expansion of high density non-adherent cells through the combined use of a cell growth chamber, a mass transfer device, or bioreactor, and a fluid circulation loop(s). Cell growth in the cell growth chamber is particularly promoted by using a cell growth chamber having a specialized shape and/or particular orientation that relies on the use of gravity to create a media-rich reservoir for cells to grow in. By vertically positioning the cell growth chamber, gravitational forces cause cells to accumulate in the lower portion of the cell growth chamber, in which such lower portion includes a media-rich reservoir for cell expansion.

According to embodiments of the present disclosure, the use of a cell growth chamber in conjunction with a mass transfer device and a fluid circulation loop creates efficiencies in cell expansion by relying on the cumulative and combined features of the devices. For example, in an embodiment, a majority of cells in the cell growth chamber are caused to settle to the bottom, or lower portion, of the cell growth chamber by gravitational forces. While some cells may exit the top portion of the cell growth chamber with the circulating media, most cells will settle into the media-rich reservoir of the lower portion of the cell growth chamber where cells can thrive and grow. Meanwhile, oxygen- and nutrient-depleted media, with some cells according to embodiments, exits the cell growth chamber. This circulating media enters the intracapillary space of the mass transfer device while fresh media, oxygenated by an oxygenator, enters the extracapillary space of the mass transfer device. The circulating media is replenished by nutrients and oxygen diffusing through the extracapillary space into the intracapillary space. Waste in the circulating media may also be diffused from the media into the extracapillary space. The replenished and cleaned media then flows through the outlet port of the mass transfer device to travel to the cell growth chamber to replenish its reservoir of media. Cells in the cell growth chamber are thus able to receive the nutrients they need for increasing expansion while remaining in the media-rich lower portion of the cell growth chamber.

Additional efficiencies are created in embodiments which rely on the cumulative and combined features of the devices. For example, the different characteristics and features of the cell growth chamber, mass transfer device, and fluid circulation loop allow for different cell types and/or sizes to flourish in environments conducive to handling their particular cell properties. In an embodiment, cells of a large diameter or weight, for example, tend to settle into the lower portion of the cell growth chamber at greater rates and at greater volumes than cells of a smaller diameter or weight.

The disclosure relates to a closed cell expansion system including a cell growth chamber, in which the cell growth chamber comprises two frustoconical shaped sections. The system also comprises a mass transfer device and a first fluid circulation loop fluidly associated with the cell growth chamber and the mass transfer device, in which non-adherent cells expand in at least two of the cell growth chamber, the mass transfer device, and the first fluid circulation loop. The non-adherent cells expand in a media that travels through the cell growth chamber, the mass transfer device, and the first fluid circulation loop.

In at least one embodiment, the two frustoconical shaped sections are joined at a maximum cross-sectional area. In at least one embodiment, the two frustoconical shaped sections taper in opposite directions toward an inlet and an outlet, in which the inlet and the outlet are disposed on opposite ends of the cell growth chamber.

In at least one embodiment, the inlet is positioned at a bottom portion of the cell growth chamber, and the cell growth chamber is oriented such that a direction of gravitational force is substantially from the outlet to the inlet. In at least one embodiment, a force of media flow from the inlet into the cell growth chamber is substantially equal to the gravitational force, in which the interaction of the force of the media flow and the gravitational force maintains the non-adherent cells in suspension in the cell growth chamber. In at least one embodiment, the cell growth chamber is formed from a unitary form. In at least one embodiment, the cell growth chamber is formed from a biocompatible polymeric material. In at least one embodiment, a semi-permeable material positioned substantially at the outlet of the cell growth chamber at least partially blocks the non-adherent cells from exiting the outlet.

In at least one embodiment, the mass transfer device comprises a housing having an intracapillary portion and an extracapillary portion. In at least one embodiment, the intracapillary portion is fluidly associated with the first fluid circulation loop. In at least one embodiment, the mass transfer device comprises an intracapillary inlet fluidly associated with an in-flow of the first circulation loop.

In at least one embodiment, the mass transfer device comprises a first end cap disposed at a first end of the housing and a second end cap disposed at a second end of the housing. In at least one embodiment, the mass transfer device comprises a plurality of hollow fibers potted to the first end cap and the second end cap. In at least one embodiment, the media flows through the plurality of the hollow fibers. In at least one embodiment, the plurality of the hollow fibers forms a membrane. In at least one embodiment, the plurality of the hollow fibers comprises a plurality of pores that allow small molecules to diffuse between the intracapillary portion and the extracapillary portion, in which the non-adherent cells are not small molecules. In at least one embodiment, the plurality of the hollow fibers is made from a biocompatible polymeric material. In at least one embodiment, the membrane allows for removal of metabolites from the media and replacement of nutrients in the media, in which the nutrients promote cell growth.

In at least one embodiment, the cell expansion system further comprises a second fluid circulation loop fluidly associated with the extracapillary portion of the mass transfer device, in which the second fluid circulation loop includes a second media that travels through the second fluid circulation loop. In at least one embodiment, the second fluid circulation loop comprises an oxygenator that adds at least a first gas to the second media. In at least one embodiment, a second gas purged from the system vents to the atmosphere via an exit port of the oxygenator. In at least one embodiment, a nutrient is introduced to the extracapillary portion of the mass transfer device through the second fluid circulation loop. In at least one embodiment, a first flow direction of the first fluid circulation loop and a second flow direction of the second fluid circulation loop are co-current.

The disclosure further relates to a closed cell expansion system, in which the system comprises a cell growth chamber having a first volume, wherein a first number of cells is grown in the first volume, and the cell growth chamber comprises two frustoconical shaped sections. The system also includes a mass transfer device comprising an intracapillary portion and an extracapillary portion, in which the intracapillary portion has a second volume, and wherein a second number of cells is grown in the second volume. The system also comprises a first fluid circulation loop fluidly associated with the cell growth chamber and the mass transfer device, in which cells expand in the cell growth chamber, the mass transfer device, and the first fluid circulation loop, and wherein the cells expand in a media that travels through the cell growth chamber, the mass transfer device, and the first fluid circulation loop, in which the first number of cells is greater than the second number of cells.

In at least one embodiment, the first and second volumes are different. In at least one embodiment, the cell growth chamber provides a reservoir of the media to promote high density cell growth. In at least one embodiment, the two frustoconical shaped sections are joined at a maximum cross-sectional area. In at least one embodiment, the two frustoconical shaped sections taper in opposite directions toward an inlet and an outlet, in which the inlet and the outlet are disposed on opposite ends of the cell growth chamber. In at least one embodiment, the inlet is positioned at a bottom portion of the cell growth chamber, in which the cell growth chamber is oriented such that a direction of gravitational force is substantially from the outlet to the inlet. In at least one embodiment, a force of media flow from the inlet into the cell growth chamber is substantially equal to the gravitational force, in which interaction of the force of the media flow and the gravitational force maintains the non-adherent cells in suspension in the cell growth chamber.

In at least one embodiment, the cell expansion system further comprises a second fluid circulation loop fluidly associated with the extracapillary portion of the mass transfer device, in which the second fluid circulation loop includes a second media that travels through the second fluid circulation loop. In at least one embodiment, the second fluid circulation loop comprises an oxygenator that adds at least one gas to the second media.

The disclosure further relates to a method of growing cells in a closed cell expansion system. The method includes the steps of providing a first volume of media in a cell growth chamber; growing a first number of cells in the first volume; fluidly associating the cell growth chamber with a mass transfer device and with a first fluid circulation loop; providing a second volume of media in an intracapillary portion of the mass transfer device; growing a second number of cells in the second volume; providing a third volume of media in the first fluid circulation loop; and growing a third number of cells in the third volume, in which the first, second, and third number of cells are different.

In at least one embodiment, the media flows through the cell growth chamber, the mass transfer device, and the first fluid circulation loop. In at least one embodiment, the method further comprises orienting the cell growth chamber such that a flow of the media is equal to and opposite in direction to a gravitational force on the cells in the cell growth chamber. In at least one embodiment, the media comprises one or more from the group consisting of: a fluid, a gas, a nutrient, a metabolite, an ion, and a lactate.

The disclosure further relates to a closed cell expansion system including a cell growth chamber, in which the cell growth chamber comprises an inlet and an outlet disposed on opposite ends of the cell growth chamber, the inlet being positioned at a bottom portion of the cell growth chamber, and the cell growth chamber being oriented such that a direction of gravitational force is substantially from the outlet to the inlet. The system further comprises a mass transfer device and a first fluid circulation loop fluidly associated with the cell growth chamber and the mass transfer device, in which non-adherent cells expand in at least two of the cell growth chamber, the mass transfer device, and the first fluid circulation loop, and wherein the non-adherent cells expand in a media that travels through the cell growth chamber, the mass transfer device, and the first fluid circulation loop.

In at least one embodiment, a force of media flow from the inlet into the cell growth chamber is substantially equal to the gravitational force, in which interaction of the force of the media flow and the gravitational force maintains the non-adherent cells in suspension in the cell growth chamber. In at least one embodiment, the cell growth chamber is formed from a biocompatible polymeric material. In at least one embodiment, a semi-permeable material positioned substantially at the outlet of the cell growth chamber partially blocks the non-adherent cells from exiting the outlet. In at least one embodiment, the mass transfer device comprises a housing having an intracapillary portion and an extracapillary portion. In at least one embodiment, the intracapillary portion is fluidly associated with the first circulation loop.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items. Further, optional steps or components are illustrated in a dashed-line format.

DETAILED DESCRIPTION

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will understand other embodiments, including improvements, that are within the spirit and scope of the present disclosure.

Embodiments of the present disclosure are generally directed toward a closed system 200 (see FIG. 3) for continuous high density cell expansion, in particular, a system for expanding non-adherent cells. A closed system means that the contents of the system are closed, or not directly exposed, to the atmosphere. The system contains at least a cell growth chamber 12 (also referred to herein as a "cell expansion chamber") and a mass transfer device 100.

Figure 1:
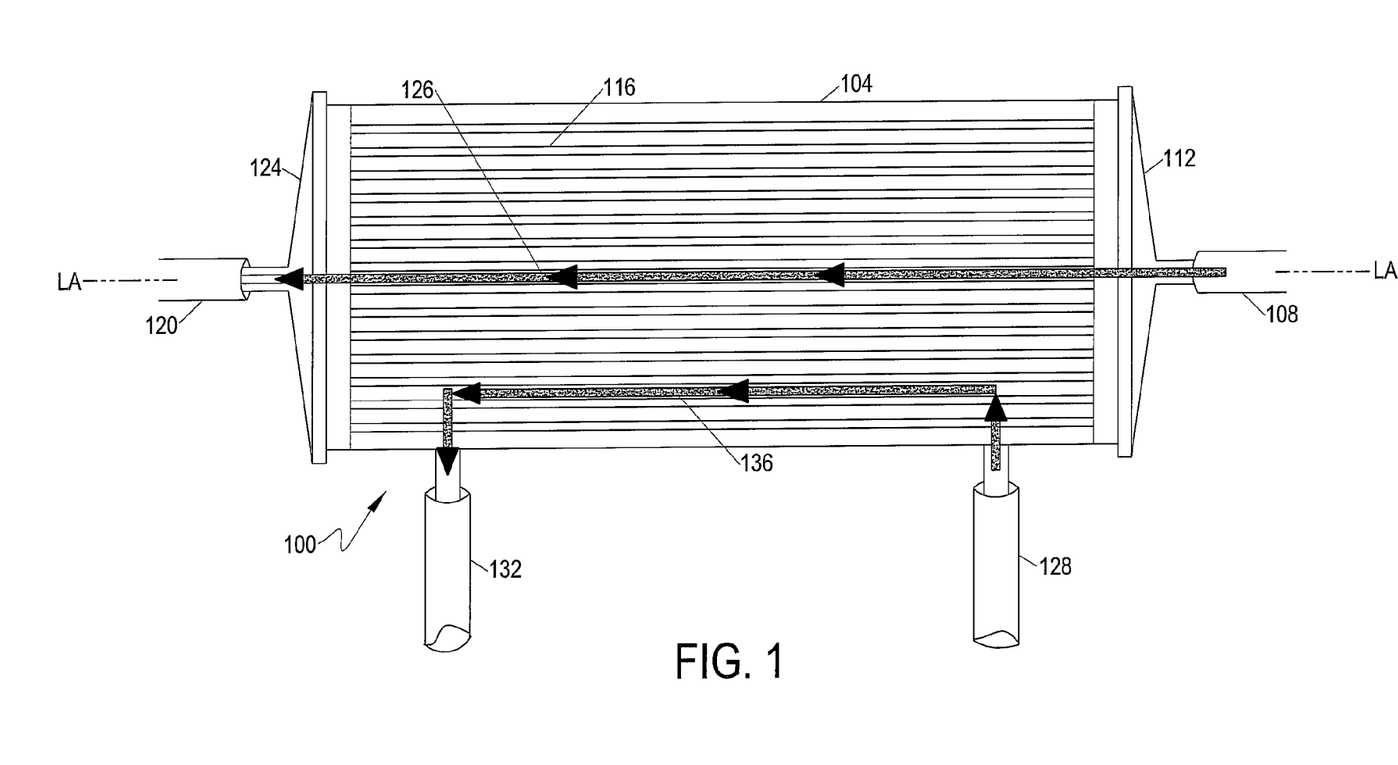
FIG. 1 is a schematic illustration of the mass transfer device in accordance with embodiments of the present disclosure.

With reference to FIG. 1, an example mass transfer device 100 which may be used with the present disclosure is shown in front side elevation view. Mass transfer device 100 has a longitudinal axis LA-LA and includes housing 104. In at least one embodiment, mass transfer device housing 104 includes four openings or ports: intracapillary (IC) inlet port 108, intracapillary (IC) outlet port 120, extracapillary (EC) inlet port 128, and extracapillary (EC) outlet port 132.

A plurality of hollow fibers 116 are disposed within mass transfer device housing 104. The material used to make the hollow fibers 116 may be any biocompatible polymeric material which is capable of being made into hollow fibers. The terms "hollow fiber," "hollow fiber capillary," and "capillary" are used interchangeably. A plurality of hollow fibers are collectively referred to as a "membrane."

In embodiments, the ends of hollow fibers 116 are potted to the ends of the mass transfer device 100 by a connective material (also referred to herein as "potting" or "potting material"). The potting can be any suitable material for binding the hollow fibers 116, provided that the flow or travel of culture media (and cells if desired) into the hollow fibers is not obstructed. Exemplary potting materials include, but are not limited to, polyurethane or other suitable binding or adhesive components. End caps 112 and 124 respectively, are disposed at each end of the mass transfer device. According to embodiments, the media includes one or more of the following, for example: a fluid, a gas, a nutrient, a metabolite, an ion, a lactate, and/or an oxygen atom, for example.

Small molecules (e.g., ions, water, oxygen, a metabolite, lactate, etc.) can diffuse through pores in the hollow fibers from the interior or IC space of the hollow fiber to the exterior or EC space, or from the EC space to the IC space, according to embodiments.

Use of a mass transfer device 100, such as the one described, allows for the simultaneous and continuous removal of waste products from the cell growth media and the replacement of nutrients in the cell growth media throughout the cell expansion process.

Figure 2:
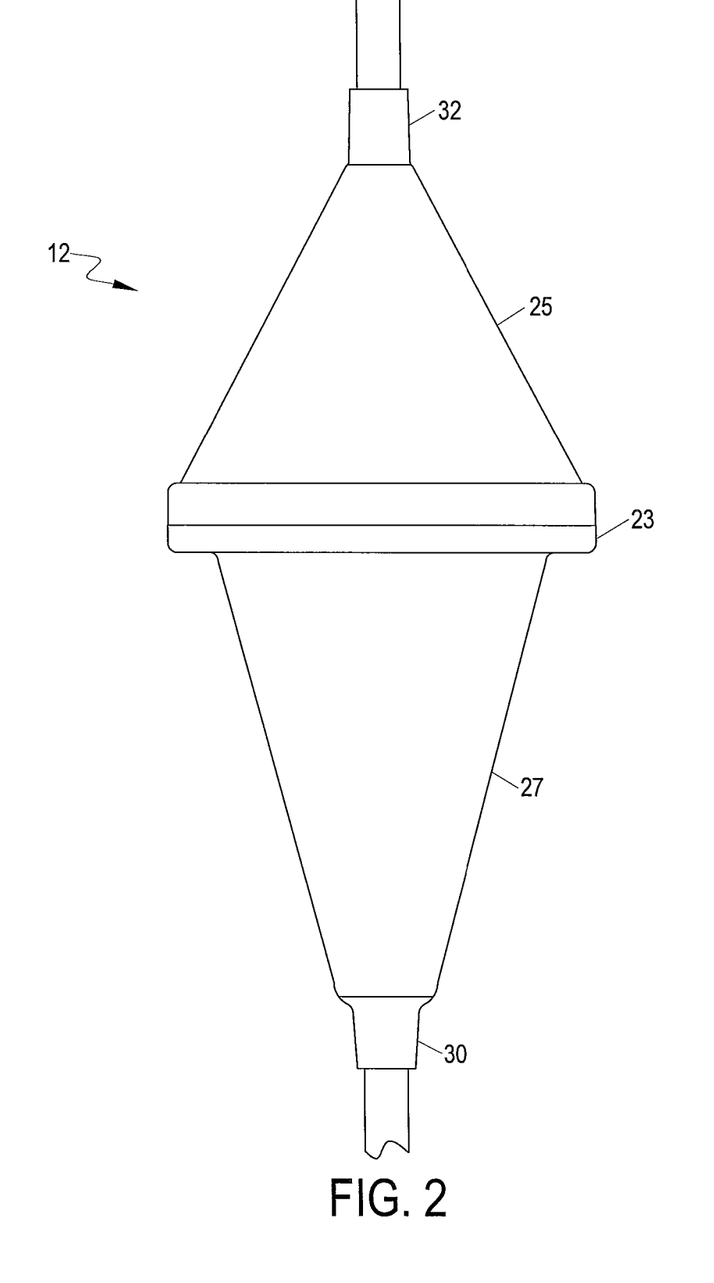
FIG. 2 is a schematic illustration of the cell growth chamber in accordance with embodiments of the present disclosure.

In embodiments, the system 200 (see FIG. 3) also includes a cell growth or cell expansion chamber 12. As shown in FIG. 2, a schematic of a possible embodiment of a cell growth chamber which may be used with the present disclosure is depicted. In an embodiment, cell growth chamber 12 includes two frustoconical shaped sections 25, 27 joined together at a maximum cross-sectional area 23 of the cell growth chamber 12. The interior of the cell growth chamber 12 tapers (decreases in cross-section) from the maximum cross-sectional area 23 in opposite directions toward inlet 30 and outlet 32. According to an embodiment, inlet 30 is positioned at the bottom, or a bottom portion, of the cell growth chamber.

The cell growth chamber 12 may be constructed from a unitary piece of plastic or from separate pieces joined together using a fixative or other sealing methods. It may be made of any biocompatible material capable of being assembled into the frustoconical shape, according to an embodiment.

The conical shape of the cell growth chamber 12 helps to keep the cells suspended within the chamber 12. The flow of media, or force of media flow, along the walls of the cell growth chamber 12 from the inlet 30 of the chamber 12 through the interior to the outlet 32 is substantially equal and opposite to the gravitational pull, or gravitational force, on the cells. In an embodiment, the flow of media along the walls of the cell growth chamber 12 from the inlet 30 of the chamber 12 through the interior to the outlet 32 is constant. The interaction of the force of the media flow and the gravitational force helps to keep the cells suspended, i.e., maintains the non-adherent cells in suspension, within the cell growth chamber 12.

The cells may be retained within the cell growth chamber 12 by blocking at least the outlet port 32 of the cell growth chamber 12 with some type of semi-permeable material which allows fluid to flow there through, yet retains cells within the chamber 12.

For non-adherent cells, the rate limiting step for cell expansion is the amount, or volume, of cell growth media available to the cells, according to embodiments. Therefore, the cell expansion chamber 12 acts not only as a place for the cells to grow, but also as a media reservoir to encourage high density cell growth by providing as much media to the cells as possible. In an embodiment, for example, a greater number of cells grows in a larger volume of media. To achieve maximal growth, the chamber should be made as large as possible, including with respect to corresponding volume, for example, within the constraints of system 200.

Figure 3:
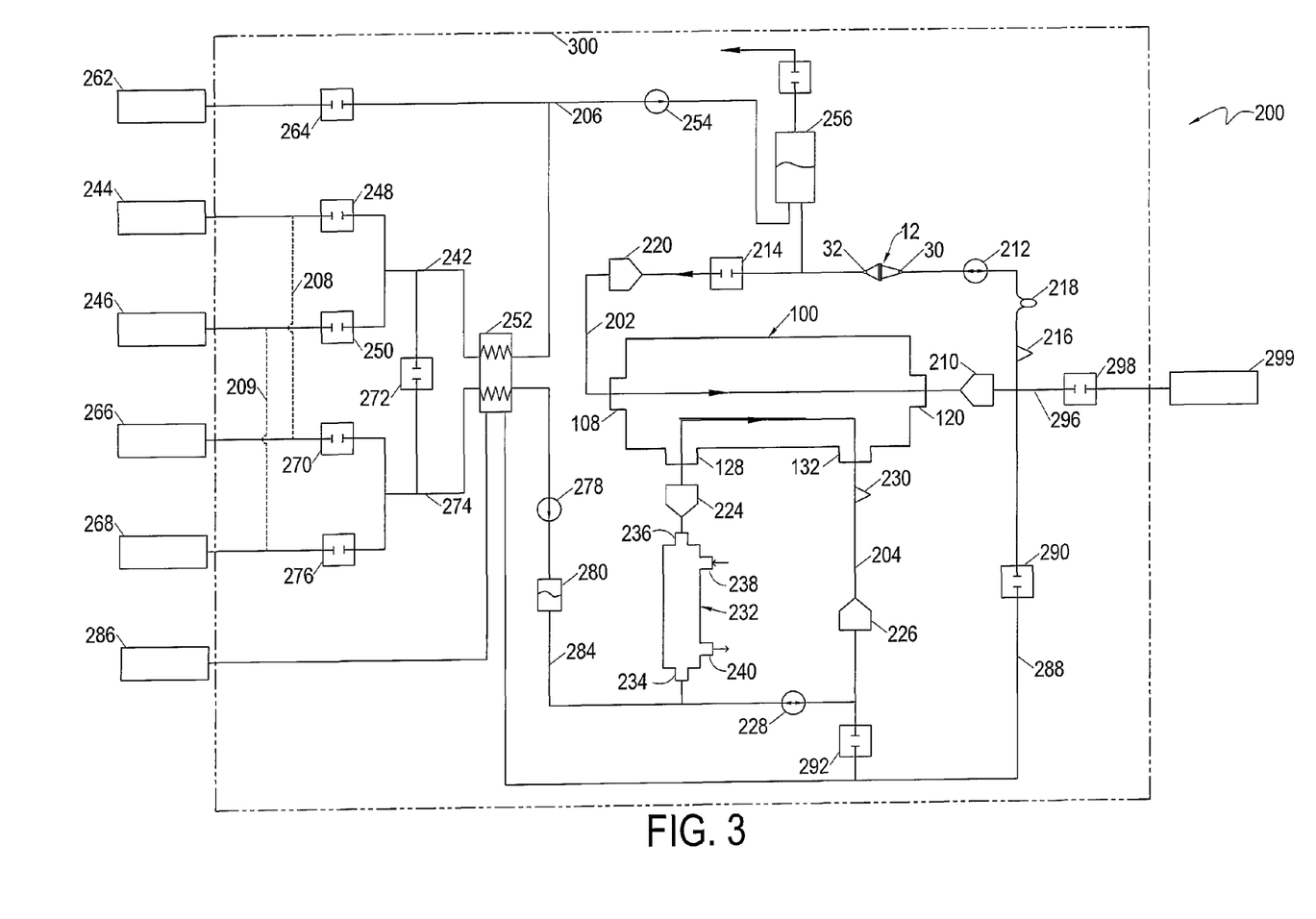
FIG. 3 is a schematic illustration of a high density cell expansion system in accordance with embodiments of the present disclosure.

In embodiments, cells may additionally be grown inside the lumen or IC space of the hollow fibers of the mass transfer device 100 and also within the associated tubing of the first fluid circulation loop 202 (see FIG. 3). In such embodiments, cells are not only grown within the cell growth chamber 12, but are also circulated throughout the first fluid circulation loop 202 in a volume of media, from the cell growth chamber 12 through the IC space of the mass transfer device 100, and back to the cell growth chamber 12. In embodiments, the volumes of media in the mass transfer device and in the first fluid circulation loop are different from the volume of media in the cell growth chamber. For example, the cell growth chamber may comprise a first volume of media, the mass transfer device may comprise a second volume of media, and the first fluid circulation loop may comprise a third volume of media. In an embodiment, the first, second and third volumes of media are different. In another embodiment, the first, second, and third volumes of media are the same.

A schematic of one possible embodiment of a cell expansion system 200 containing both the mass transfer device 100 and the cell growth chamber 12 as described above is shown in FIG. 3.

First fluid flow path 206 is fluidly associated with mass transfer device 100 and cell growth chamber 12 to form first fluid circulation path 202 (also referred to herein as the "intracapillary loop" or "IC loop" or "first fluid circulation loop"). In an embodiment, a single mass transfer device 100 and cell growth chamber 12 are used. In another embodiment, multiple mass transfer devices and multiple cell growth chambers are used. Fluid flows or travels into mass transfer device 100 through inlet port 108, and exits via outlet port 120. The fluid path between the inlet port 108 and the outlet port 120 defines the intracapillary portion 126 of the mass transfer device (see FIG. 1). The intracapillary inlet 108 is fluidly associated with an in-flow of the first fluid circulation loop 202. Fluid flows into cell growth chamber 12 through inlet port 30 and exits via outlet port 32. It should be noted that the cell growth chamber may be located anywhere within the IC loop. Pressure gauge 210 measures the pressure of media leaving mass transfer device 100 and entering cell growth chamber 12. IC circulation pump 212 controls the rate of media flow through first fluid circulation loop 202. Media entering the IC loop may enter through valve 214. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the cell expansion system, and modifications to the schematic shown are within the scope of embodiments of the present disclosure.

Samples of media can be obtained from a sample port 216 or a sample coil 218 during operation. Pressure/temperature gauge 220 allows measurement of media pressure and temperature during operation.

Cells grown/expanded in cell growth chamber 12 or in the entire IC loop 202 including mass transfer device 100 can be flushed out of the IC loop 202 into harvest bag 299 through valve 298.

Fluid in second fluid circulation path 204 (also referred to herein as the "extracapillary loop" or "EC loop" or "second fluid circulation loop") enters mass transfer device 100 via EC inlet port 128, and leaves mass transfer device 100 via EC outlet port 132. The fluid path between the EC inlet port 128 and the EC outlet port 132 defines the EC portion 136 of the mass transfer device 100 (see FIG. 1).

Pressure/temperature gauge 224 measures the pressure and temperature of the media before the media enters the EC space of the mass transfer device 100. Pressure gauge 226 measures the pressure of media after it leaves the mass transfer device 100. Samples of media can be obtained from sample port 230 or a sample coil (not shown) during operation, according to embodiments.

After leaving EC outlet port 132 of mass transfer device 100, fluid in second fluid circulation path 204 passes through EC circulation pump 228 to oxygenator 232. Media flows into oxygenator 232 via inlet port 234, and exits oxygenator 232 via outlet port 236. Oxygenator 232 adds oxygen and other gases, as desired, to the media. The oxygenator 232 can be any appropriately sized oxygenator known in the art. Gas flows into oxygenator 232 via inlet port 238 and out of oxygenator 232 through outlet port 240. Filters (not shown) may be associated with ports 238 and 240 respectively to reduce or prevent contamination of oxygenator 232 and associated media. Air or gas purged from the system 200 can vent to the atmosphere via exit port 240 of oxygenator 232.

In the configuration depicted in FIG. 3, fluid media in first fluid circulation path 202 and second fluid circulation path 204 flows through mass transfer device 100 in the same direction (a co-current configuration). However, cell expansion system 200 can also be configured to flow fluid in an opposite or counter-current direction.

In an embodiment, cells (from bag 262) to be expanded and IC media from bag 246 are introduced to first fluid circulation path 202 via a valve(s). In an embodiment, valve 264 and/or valve 250 may be used, respectively, for example. Fluid containers 244 (reagent) and 246 (IC media) may be fluidly associated with either first fluid inlet path 242 via valves 248 and 250, respectively, or second fluid inlet path 274 via valves 270 and 276. First and second sterile sealable input priming paths 208 and 209 are provided. In embodiments, air removal chamber 256 is fluidly associated with first fluid circulation path 202.

According to embodiments of the present disclosure, EC media (from bag 268) or wash solution ((if used) from bag 266) may be added to either the first or second fluid flow path. Fluid container 266 may be fluidly associated with valve 270 that is fluidly associated with first fluid circulation path 202 via distribution valve 272 and first fluid inlet path 242. Alternatively, fluid container 266 can be fluidly associated with second fluid circulation path 204 via second fluid inlet path 274 and second fluid flow path 284 by opening valve 270 and closing distribution valve 272. Likewise, fluid container 268 is fluidly associated with valve 276 that may be fluidly associated with first fluid circulation path 202 via first fluid inlet path 242 and distribution valve 272. Alternatively, fluid container 268 may be fluidly associated with second fluid inlet path 274 by opening valve 276 and closing distribution valve 272.

An optional heat exchanger 252 may be provided to warm media, reagent or wash solution.

In the IC loop 202, fluid is initially advanced by the IC inlet pump 254. In the EC loop 204, fluid is initially advanced by the EC inlet pump 278. An air detector 280, such as an ultrasonic sensor, may also be associated with the EC inlet path 284, according to embodiments.

First and second fluid circulation paths 202 and 204 are connected to waste line 288. When valve 290 is opened, IC media can flow through waste line 288 to waste bag 286. Likewise, when valve 292 is opened, EC media can flow through waste line 288 to waste bag 286.

In accordance with embodiments of the present disclosure, expanded cells are harvested via cell harvest path 296. Here, cells from cell expansion chamber 12 and, optionally, mass transfer device 100 and associated tubing can be harvested from the IC loop by pumping the IC media containing the cells through cell harvest path 296 and valve 298 to cell harvest bag 299.

In embodiments, various components of the cell expansion system 200 are contained or housed within an incubator 300, wherein the incubator maintains cells and media at a desirable temperature. The size of cell growth chamber 12, and the volume of media it may contain, for example, is dependent upon the size of the incubator, according to embodiments. However, in other embodiments, the cell expansion system 200 may be placed in a larger temperature controlled space such as a warm room, in which case the size of the cell growth chamber 12 is not necessarily limited and may have a range of possible dimensions.

As consistent with FIGS. 1, 2, and 3 described above, FIG. 4 provides example operational steps 302 for growing cells in a cell expansion system, in accordance with embodiments of the present disclosure. START operation 304 is initiated, and process 302 proceeds to provide 306 a first volume of media in a cell growth chamber. In an embodiment, such first volume is controlled by the size of the cell growth chamber. In another embodiment, one or more pumps and/or one or more valves, as described above, may control the amount of the first volume of media. A first number of cells is then grown 308 in the first volume. Next, process 302 proceeds to fluidly associate 310, 312 the cell growth chamber with a mass transfer device and a first fluid circulation loop, as described above according to embodiments.

Figure 4:
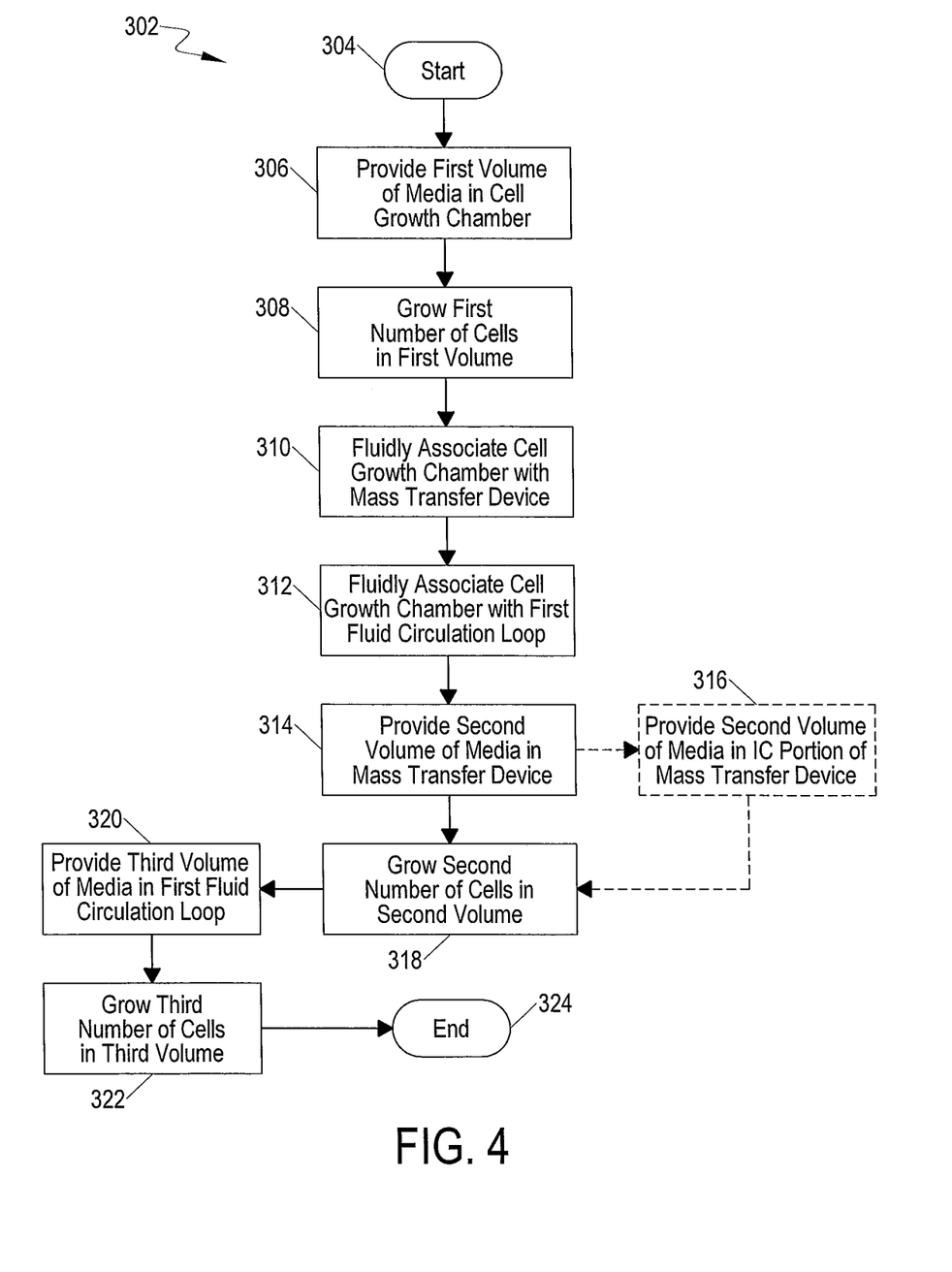
FIG. 4 depicts a flow diagram showing the operational characteristics of a process for growing cells in a cell expansion system in accordance with embodiments of the present disclosure.

Proceeding to operation 314, a second volume of media is provided in the mass transfer device, according to embodiments described above. In an embodiment, such second volume is controlled by the size of the mass transfer device. In another embodiment, one or more pumps and/or one or more valves, as described above, may control the amount of the second volume of media. In an embodiment, such second volume of media is in an intracapillary portion of the mass transfer device, as shown by optional step 316. Next, process 302 proceeds to operation 318, in which a second number of cells is grown in the second volume.

In an embodiment, a third volume of media is provided 320 in the first fluid circulation loop, as described above in accordance with embodiments of the present disclosure. In an embodiment, such third volume is controlled by the size of the first circulation loop. In another embodiment, one or more pumps and/or one or more valves, as described above, may control the amount of the third volume of media. Next, a third number of cells is grown in the third volume of media 322. In an embodiment, process 302 then terminates at END operation 324.

With respect to the process illustrated in FIG. 4, the operational steps depicted are offered for purposes of illustration and may be rearranged, combined into other steps, used in parallel with other steps, etc., according to embodiments of the present disclosure. Further, fewer or additional steps may be used in embodiments without departing from the spirit and scope of the present disclosure.

It will be apparent to those skilled in the art that various modifications may be made to the apparatus, systems, and methods described herein. Thus, it should be understood that the embodiments are not limited to the subject matter discussed in the Specification. Rather, the present disclosure is intended to cover modifications, variations, and/or equivalents. The acts, features, structures, and/or media are disclosed as illustrative embodiments for implementation of the claims. The invention is defined by the appended claims.

What is claimed is:

1. A closed cell expansion system, comprising:
a cell growth chamber, wherein the cell growth chamber comprises two frustoconical shaped sections joined together to form the cell growth chamber, wherein the two frustoconical shaped sections are joined together at a maximum cross-sectional area of the cell growth chamber to form an interior for growing and suspending cells, wherein walls of the interior taper from the maximum cross-sectional area of the cell growth chamber in opposite directions toward an inlet and an outlet of the cell growth chamber, wherein the inlet and the outlet are disposed on opposite ends of the cell growth chamber, wherein the walls of the interior taper to help keep the cells suspended within the cell growth chamber, and wherein the interior of the cell growth chamber comprises a first volume;
a mass transfer device, wherein a plurality of hollow fibers are disposed within a housing of the mass transfer device, the housing comprising an intracapillary portion and an extracapillary portion, and wherein the intracapillary portion comprises a second volume, the second volume being different from the first volume; and
a first fluid circulation loop fluidly associated with the cell growth chamber and the mass transfer device, wherein non-adherent cells expand in at least two of the cell growth chamber, the mass transfer device, and the first fluid circulation loop, and wherein the non-adherent cells expand in a media that travels through the cell growth chamber, the mass transfer device, and the first fluid circulation loop.

2. The cell expansion system of claim 1, wherein the inlet is positioned at a bottom portion of the cell growth chamber, and wherein the cell growth chamber is oriented such that a direction of gravitational force is from the outlet to the inlet.

3. The cell expansion system of claim 2, wherein a force of media flow from the inlet into the cell growth chamber is equal to the gravitational force, and wherein interaction of the force of media flow and the gravitational force maintains the non-adherent cells in suspension in the cell growth chamber.

4. The cell expansion system of claim 1, wherein the cell growth chamber is formed from a biocompatible polymeric material.

5. The cell expansion system of claim 1, wherein a semipermeable material positioned at the outlet of the cell growth chamber at least partially blocks the non-adherent cells from exiting the outlet.

6. The cell expansion system of claim 1, wherein the intracapillary portion is fluidly associated with the first fluid circulation loop.

7. The cell expansion system of claim 6, wherein the mass transfer device comprises an intracapillary inlet fluidly associated with an in-flow of the first fluid circulation loop.

8. The cell expansion system of claim 7, wherein the mass transfer device comprises a first end cap disposed at a first end of the housing and a second end cap disposed at a second end of the housing.

9. The cell expansion system of claim 8, wherein the plurality of hollow fibers are potted to the first end cap and the second end cap of the mass transfer device.

10. The cell expansion system of claim 9, wherein the media flows through the plurality of the hollow fibers.

11. The cell expansion system of claim 10, wherein the plurality of the hollow fibers forms a membrane.

12. The cell expansion system of claim 11, wherein the plurality of the hollow fibers comprises a plurality of pores that allow small molecules to diffuse between the intracapillary portion and the extracapillary portion, and wherein the non-adherent cells are not small molecules.

13. The cell expansion system of claim 12, wherein the plurality of the hollow fibers is made from a biocompatible polymeric material.

14. The cell expansion system of claim 13, wherein the membrane allows for removal of metabolites from the media and replacement of nutrients in the media, and wherein the nutrients promote cell growth.

15. The cell expansion system of claim 1, further comprising a second fluid circulation loop fluidly associated with the extracapillary portion of the mass transfer device, wherein the second fluid circulation loop includes a second media that travels through the second fluid circulation loop.

16. The cell expansion system of claim 15, wherein the second fluid circulation loop comprises an oxygenator that adds at least a first gas to the second media.

17. The cell expansion system of claim 15, wherein a nutrient is introduced to the extracapillary portion of the mass transfer device through the second fluid circulation loop.

18. The cell expansion system of claim 17, wherein a first flow direction of the first fluid circulation loop and a second flow direction of the second fluid circulation loop are co-current.

19. A closed cell expansion system, comprising:
a cell growth chamber having a first volume, wherein a first number of cells is grown in the first volume, wherein the cell growth chamber comprises two frustoconical shaped sections joined together to form the cell growth chamber, wherein the two frustoconical shaped sections are joined together at a maximum cross-sectional area of the cell growth chamber to form an interior, wherein walls of the interior taper from the maximum cross-sectional area of the cell growth chamber in opposite directions toward an inlet and an outlet of the cell growth chamber, wherein the inlet and the outlet are disposed on opposite ends of the cell growth chamber, wherein the walls of the interior taper to help keep the cells suspended within the cell growth chamber, and wherein the interior of the cell growth chamber comprises the first volume;
a mass transfer device, wherein a plurality of hollow fibers are disposed within a housing of the mass transfer device, the housing comprising an intracapillary portion and an extracapillary portion, wherein the intracapillary portion comprises a second volume, and wherein a second number of cells is grown in the second volume; and
a first fluid circulation loop fluidly associated with the cell growth chamber and the mass transfer device, wherein cells expand in the cell growth chamber, the mass transfer device, and the first fluid circulation loop, and wherein the cells expand in a media that travels through the cell growth chamber, the mass transfer device, and the first fluid circulation loop, and wherein the first number of cells is greater than the second number of cells.

20. The cell expansion system of claim 19, wherein the first and second volumes are different.

21. The cell expansion system of claim 19, wherein the cell growth chamber provides a reservoir of the media to promote high density cell growth.

22. The cell expansion system of claim 19, wherein the inlet is positioned at a bottom portion of the cell growth chamber, and wherein the cell growth chamber is oriented such that a direction of gravitational force is from the outlet to the inlet.

23. The cell expansion system of claim 22, wherein a force of media flow from the inlet into the cell growth chamber is equal to the gravitational force, and wherein interaction of the force of media flow and the gravitational force maintains non-adherent cells in suspension in the cell growth chamber.

24. The cell expansion system of claim 19, further comprising a second fluid circulation loop fluidly associated with the extracapillary portion of the mass transfer device, wherein the second fluid circulation loop includes a second media that travels through the second fluid circulation loop.

25. The cell expansion system of claim 24, wherein the second fluid circulation loop comprises an oxygenator that adds at least one gas to the second media.

* * * * *